(12) United States Patent
Jaillon et al.

(10) Patent No.: US 10,052,400 B2
(45) Date of Patent: Aug. 21, 2018

(54) METHOD FOR PREPARING NEUTRALIZED MATRIX OF NON-ANTIGENIC COLLAGENOUS MATERIAL

(71) Applicant: Sofradim Production, Trévoux (FR)

(72) Inventors: Amandine Jaillon, Lyons (FR); Aurelie Serrero, Lyons (FR)

(73) Assignee: Sofradim Production, Trévoux (FR)

( * ) Notice: Subject to any disclaimer, the term of this patent is extended or adjusted under 35 U.S.C. 154(b) by 2 days.

(21) Appl. No.: 15/314,741

(22) PCT Filed: Jun. 1, 2015

(86) PCT No.: PCT/EP2015/062169
§ 371 (c)(1),
(2) Date: Nov. 29, 2016

(87) PCT Pub. No.: WO2015/181395
PCT Pub. Date: Dec. 3, 2015

(65) Prior Publication Data
US 2017/0189574 A1  Jul. 6, 2017

(30) Foreign Application Priority Data
May 30, 2014  (EP) .................................... 14305809

(51) Int. Cl.
*A61L 15/00* (2006.01)
*A61L 27/24* (2006.01)
(Continued)

(52) U.S. Cl.
CPC ............ *A61L 15/325* (2013.01); *A61L 27/24* (2013.01); *A61L 27/3683* (2013.01); *A61L 27/50* (2013.01); *A61L 2400/04* (2013.01)

(58) Field of Classification Search
CPC .............................. A61L 15/325; A61L 27/24
See application file for complete search history.

(56) References Cited

U.S. PATENT DOCUMENTS 3,810,473 A   5/1974  Cruz, Jr. et al.
3,919,773 A  11/1975  Freeman
(Continued)

FOREIGN PATENT DOCUMENTS

GB          1565340 A      4/1980
WO     WO 85/05274 A1    12/1985
(Continued)

OTHER PUBLICATIONS

O'Brien, F. J. et al., "Influence of freezing rate on pore structure in freeze-dried collagen-GAG scaffolds" Biomaterials, Mar. 2004, pp. 1077-1086, vol. 25, Issue 6.
(Continued)

*Primary Examiner* — Benjamin Packard

(57) ABSTRACT

The present invention relates to a method for preparing a neutralized matrix of non-antigenic collagenous material comprising the steps of: —a) preparing an acidic solution of non-antigenic collagenous material, —b) pouring the solution of a) into a mold in order to form a layer, —c) lyophilizing the layer of b) in order to obtain an acidic matrix of non-antigenic collagenous material, d) sterilizing the acidic matrix obtained in c) with ethylene oxide in order to obtain a neutralized matrix of non-antigenic collagenous material. The invention also relates to the matrices obtained and to surgical implants comprising such matrices.

18 Claims, 1 Drawing Sheet

(51) Int. Cl.
*A61L 15/32* (2006.01)
*A61L 27/36* (2006.01)
*A61L 27/50* (2006.01)

(56) References Cited

U.S. PATENT DOCUMENTS

| | | |
|---|---|---|
| 4,534,761 A | 8/1985 | Raible |
| 4,970,298 A | 11/1990 | Silver et al. |
| 4,986,831 A | 1/1991 | King et al. |
| 5,002,583 A | 3/1991 | Pitaru et al. |
| 5,192,311 A | 3/1993 | King et al. |
| 5,397,353 A | 3/1995 | Oliver et al. |
| 5,496,371 A | 3/1996 | Eppley et al. |
| 5,676,967 A | 10/1997 | Williams et al. |
| 5,785,983 A | 7/1998 | Furlan et al. |
| 6,001,895 A | 12/1999 | Harvey et al. |
| 6,004,333 A | 12/1999 | Sheffield et al. |
| 6,015,844 A | 1/2000 | Harvey et al. |
| 6,153,292 A | 11/2000 | Bell et al. |
| 6,262,332 B1 | 7/2001 | Ketharanathan |
| 6,277,397 B1 | 8/2001 | Shimizu |
| 6,323,278 B2 | 11/2001 | Rhee et al. |
| 6,342,484 B1 | 1/2002 | Kulkarni et al. |
| 6,368,859 B1 | 4/2002 | Atala |
| 6,440,167 B2 | 8/2002 | Shimizu |
| 6,534,591 B2 | 3/2003 | Rhee et al. |
| 6,537,313 B2 | 3/2003 | Ketharanathan |
| 6,599,323 B2 | 7/2003 | Melican et al. |
| 6,645,250 B2 | 11/2003 | Schuller |
| 6,695,855 B1 | 2/2004 | Gaston |
| 6,699,470 B1 | 3/2004 | Ameer et al. |
| 6,736,823 B2 | 5/2004 | Darois et al. |
| 6,773,440 B2 | 8/2004 | Gannoe et al. |
| 6,833,408 B2 | 12/2004 | Sehl et al. |
| 6,852,330 B2 | 2/2005 | Bowman et al. |
| 6,884,428 B2 | 4/2005 | Binette et al. |
| 6,936,271 B1 | 8/2005 | Oliver et al. |
| 7,044,982 B2 | 5/2006 | Milbocker |
| 8,142,515 B2 | 3/2012 | Therin et al. |
| 2001/0053839 A1 | 12/2001 | Noishiki et al. |
| 2002/0127265 A1 | 9/2002 | Bowman et al. |
| 2003/0149173 A1 | 8/2003 | Rhee et al. |
| 2003/0193104 A1 | 10/2003 | Melican et al. |
| 2003/0203485 A1 | 10/2003 | Takezawa et al. |
| 2004/0013712 A1 | 1/2004 | Parma |
| 2004/0037866 A1 | 2/2004 | Semertzides et al. |
| 2004/0093069 A1 | 5/2004 | Priewe et al. |
| 2004/0105880 A1 | 6/2004 | Turner et al. |
| 2004/0181288 A1 | 9/2004 | Darois et al. |
| 2004/0185085 A1 | 9/2004 | Ochi et al. |
| 2004/0192658 A1 | 9/2004 | Hunter et al. |
| 2004/0231678 A1 | 11/2004 | Fierro |

FOREIGN PATENT DOCUMENTS

| | | |
|---|---|---|
| WO | WO 2006/096027 A1 | 9/2006 |
| WO | WO 2013/116744 A1 | 8/2013 |

OTHER PUBLICATIONS

Doillon, C.J., et al., "Collagen-based wound dressings: Control of the pore structure and morphology," J. Biomed. Mater. Res., Oct. 1986, vol. 20(8).
Schoof, H. et al., Control of Pore Structure and Size in Freeze-Dried Collagen Sponges, Journal of Biomedical Materials Research, May 2001, pp. 352-357, vol. 58, No. 4.
International Search Report for PCT/EP15/062169 date of completion is Jul. 21, 2015 (2 pages).

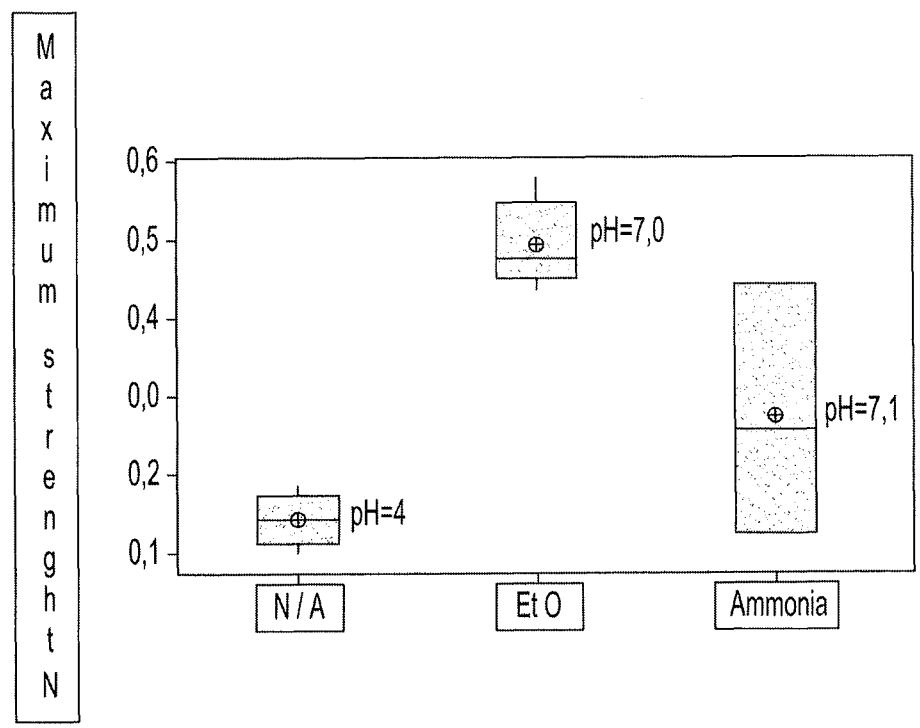

METHOD FOR PREPARING NEUTRALIZED MATRIX OF NON-ANTIGENIC COLLAGENOUS MATERIAL

CROSS-REFERENCE TO RELATED APPLICATIONS

This application is a National Stage Application of PCT/EP15/062169 filed Jun. 1, 2015, which claims benefit of and priority to European Patent Application Serial No. 14305809.7 filed May 30, 2014, the disclosure of the above-identified application is hereby incorporated by reference in its entirety.

The present invention relates to a method for preparing neutralized matrices of non-antigenic collagenous material showing good tensile strength. The invention further relates to matrices obtained by this method and to surgical implants, for example hernia repair implants or haemostats, comprising such matrices.

Collagen based matrices in general are particularly useful for the manufacture of implants in the medical field. Such matrices are usually obtained by lyophilisation of a collagen solution. Lyophilization involves a first step during which a solution is frozen in a particular structure, and then a second step, during which a controlled pressure is applied in order to cause sublimation of the water present in the frozen structure. At the end of the sublimation step, only the constituents present in the initial solution remain, thus producing a porous structure.

Indeed, the porous structure of such collagen matrices is of particular interest in the manufacture of surgical implants for many reasons. When the implant is intended to repair a tissue defect, for example in the case of a hernia in the abdominal wall, a porous structure favors cell colonization and therefore reconstruction of the biological tissue. Alternatively, when the implant is intended to be used as a haemostatic patch, in order to stop bleeding, the porous structure allows efficiently absorbing biological fluids, like blood.

Nevertheless, these reinforcing implants and haemostatic patches must also show very good mechanical properties, such as a high tensile strength, and good handling characteristics.

Various collagenous preparations have been suggested for the manufacture of surgical implants. These preparations have comprised dispersions, solutions and gels of collagen, as well as reconstituted and spongy forms of collagen. These preparations were most often prepared by digesting collagen of animal origin with a proteolytic enzyme active under acidic conditions. The collagenous material is solubilised in the acidic media and can be filtered from any debris and insoluble skin components. The solubilised collagen may be reconstituted as a solid, gel or sponge by raising the pH of the solution and stabilising by cross-linking. However, the natural structure of the collagen is lost in the process. The resulting preparations tend to have little or no tensile strength, are amorphous in structure and show a propensity for being reabsorbed, either disappearing from the site of injection or implantation or being replaced by scar tissue.

A different class of collagenous materials, herein after called "non-antigenic collagenous material" in the present application, are those in which the basic structure of the natural collagen, for example from skin, is maintained, which are substantially free of antigenic non-fibrous tissue proteins and which are substantially free of antigenic polysaccharides, mucopolysaccharides and glycoproteins. The preparation of such non-antigenic collagenous materials is described in GB 1 565 340, U.S. Pat. No. 5,397,353 and U.S. Pat. No. 6,936,271.

In the present application, by "material substantially free of a compound" is meant that the material contains less than 5%, preferably less than 1% in weight of said compound.

The preparation of non-antigenic collagenous material may comprise treating fibrous tissue of human or animal origin with two enzymes, one of said enzymes being a proteolytic enzyme which will under certain conditions remove the non-fibrous tissue proteins, and the other of said enzymes being a carbohydrate-splitting enzyme which will under certain conditions remove antigenic polysaccharide, mucopolysaccharides and glycoproteins from the tissue. Non-antigenic collagenous material, in particular obtained as described above, has low or absent antigenicity. Any residual antigenicity in the tissue may be removed therefrom by reacting it with a cross-linking agent which will under certain conditions form a link between the terminal amino groups of lysine groups in the tissue. Crosslinking agents may be glutaraldehyde, formalaldehyde and nitrous acid.

When homografted between individuals of the same species or heterografted between individuals of a different species, non-antigenic collagenous material does not elicit immunological rejection reactions or foreign body reactions. Non-antigenic collagenous material is particularly stable and strong. In addition, the original architecture of the collagenous fibrous material is preserved. In particular, in a non-antigenic collagenous material, the telopeptides of the collagen are kept intact. The material is neither solubilised nor denatured in the process so its natural structure is maintained which makes an implant derived from the material feel natural rather than an inert material.

Non-antigenic collagenous material is capable of being infiltrated and colonized by the host cells of another individual of the same or different species and revascularized to form a repair implant for example.

Non-antigenic collagenous material may be prepared under the form of a sheet material, of a cryomilled powder or also as a powdered lyophilised form.

Non-antigenic collagenous material is therefore of particular interest for surgical applications. It would be interesting to provide matrices of non-antigenic collagenous material in order to use them in the manufacture of surgical implants, such as for example hernia repair implants or haemostatic patches.

Anyway, in order to manufacture matrices of non-antigenic collagenous material, a solution of such material must be prepared and then lyophilised.

Non-antigenic collagenous material, regardless from the form under which it is prepared, is not soluble at neutral pH and may be solubilised in an acidic solution only. The matrices obtained by lyophilisation of these acidic solutions are also acidic.

It has been observed that, when put in neutral aqueous conditions, the acidic matrices of non-antigenic collagenous material dissolve completely. These re-solubilizations result in the total destruction of the matrix which can therefore no longer be used in the manufacture of a reinforcement implant or of a haemostatic patch. The acidic matrix may neither be used as a finished product by a surgeon in this state because it would not fulfil its function. Indeed, the acidic matrix of non-antigenic collagenous material loses all mechanical strength once put in the medium, such as biological fluids, in which it is intended to be implanted.

In addition, acidic matrices may cause biocompatibility problems with adjacent biological tissue once implanted in a patient body.

It would be desirable to provide a method for preparing matrices of non-antigenic collagenous material capable of maintaining their handling characteristics when put in contact with a neutral medium such as biological fluids, so that such matrices may be used in the manufacture of implants such as hernia repair implants or haemostatic patches.

In particular, it would be desirable to implement a method of preparing matrices of non-antigenic collagenous material that would make it possible to efficiently neutralize such matrices in order to prepare effective surgical implants for reinforcing abdominal walls for example or for haemostatic purposes.

The Applicant has found that by performing a specific sterilization step on matrices obtained by lyophilisation of an acidic solution of non-antigenic collagenous material, it was possible to efficiently neutralize and sterilize such matrices at the same time, while enhancing their mechanical properties, in particular their tensile strength.

A first aspect of the present invention is a method for preparing a neutralized matrix of non-antigenic collagenous material comprising the steps of:
 a) preparing an acidic solution of non-antigenic collagenous material,
 b) pouring the solution of a) into a mould in order to form a layer,
 c) lyophilizing the layer of b) in order to obtain an acidic matrix of non-antigenic collagenous material,
 d) sterilizing the acidic matrix obtained in c) with ethylene oxide in order to obtain a neutralized matrix of non-antigenic collagenous material.

The method according to the invention makes it possible to obtain neutralized matrices of non-antigenic collagenous material showing excellent mechanical properties such as tensile strength. In particular, the method of the invention allows performing the neutralization and the sterilization of the matrices in a single step. The method of the invention allows therefore saving at least one step in the manufacturing process of a collagen matrices, namely of a matrix of non-antigenic collagenous material. The manufacturing process is therefore rendered particularly simple. Time is saved and opportunities of making mistakes are decreased with respect to a method where the neutralization step and the sterilization step are two separate steps. The matrices of non-antigenic collagenous material obtained by means of the method according to the invention have excellent tensile strength. They also show good handling characteristics. They therefore make it possible to obtain particularly effective surgical implants, for example for reinforcing the abdominal wall. The matrices obtained by the method of the invention are also particularly useful in the manufacture of haemostats such as haemostatic patches. The matrices obtained by the method of the invention may also be used as scaffolds for cell culture. The matrices obtained by the method of the invention may be used on their own or in combination with a textile or with any other element, such as for example a film, a matrix of same or different composition.

Another aspect of the invention is a matrix obtained by the method of the invention. The matrices obtained by the method of the invention show in particular a tensile strength much greater than that of matrices prepared according to steps a)-c) above but which have not been sterilized according to step d). An aspect of the invention is therefore a neutralized matrix of non-antigenic collagenous material obtained by the method of the invention. An aspect of the invention is a neutralized matrix of non-antigenic collagenous material obtained by the method of the invention, having a tensile strength, for example measured according to standard ASTM D0638-03 with type IV specimen, at least two times greater, preferably three times greater, than that of the non sterilized matrix.

According to a first step of the method according to the invention, step a), an acidic solution of non-antigenic collagenous material is prepared.

As seen above, "non-antigenic collagenous material" in the present application, means a collagenous material in which the basic structure of the natural collagen, for example from skin, is maintained, which is substantially free of antigenic non-fibrous tissue proteins and which is substantially free of antigenic polysaccharides, mucopolysaccharides and glycoproteins. The preparation of such non-antigenic collagenous materials is described in GB 1 565 340, U.S. Pat. No. 5,397,353 and U.S. Pat. No. 6,936,271.

In the present application, by "material substantially free of a compound" is meant that the material contains less than 5%, preferably less than 1% in weight of said compound.

The preparation of non-antigenic collagenous material may comprise treating fibrous tissue of human or animal origin with two enzymes, one of said enzymes being a proteolytic enzyme which will under certain conditions remove the non-fibrous tissue proteins, and the other of said enzymes being a carbohydrate-splitting enzyme which will under certain conditions remove antigenic polysaccharide, mucopolysaccharides and glycoproteins from the tissue. Non-antigenic collagenous material, in particular obtained as described above, has low or absent antigenicity. Any residual antigenicity in the tissue may be removed therefrom by reacting it with a cross-linking agent which will under certain conditions form a link between the terminal amino groups of lysine groups in the tissue. Crosslinking agents may be glutaraldehyde, formalaldehyde and nitrous acid.

When homografted between individuals of the same species or heterografted between individuals of a different species, non-antigenic collagenous material does not elicit immunological rejection reactions or foreign body reactions. Non-antigenic collagenous material is particularly stable and strong. In addition, the original architecture of the collagenous fibrous material is preserved. In particular, in a non-antigenic collagenous material, the telopeptides of the collagen are kept intact. The material is neither solubilised nor denatured in the process so its natural structure is maintained which makes an implant derived from the material feel natural rather than an inert material.

Non-antigenic collagenous material is capable of being infiltrated and colonized by the host cells of another individual of the same or different species and revascularized to form a repair implant for example.

Non-antigenic collagenous material may be prepared under the form of a sheet material, of a cryomilled powder or also as a powdered lyophilised form.

Non-antigenic collagenous material may also preferably be substantially free of cellular elements. In this view, the fibrous tissue is purified so that all cellular elements such as sweat glands, sebaceous glands and vascular tissue are removed thus eliminating cyst formation and foreign body reactions when subsequently implanted in a body. Such a purification process is described in U.S. Pat. No. 5,397,353.

Non-antigenic collagenous material may also preferably be substantially free of lipids and lipid residues. In this view, the fibrous tissue may be further treated in order to remove the lipid portions from the tissue, for example by using a selective enzyme such as a lipase or alternatively by solvent extraction using an organic solvent. Such a process for removing the lipids and lipid residues from the non-antigenic collagenous material is described in U.S. Pat. No. 5,397,353.

The fibrous tissue may further be treated by polyisocyanates in order to obtain non-antigenic collagenous material preparations having particularly low cytotoxicity. Such non-antigenic collagenous material shows a good inertness with respect to adjacent biological tissue when implanted.

Non-antigenic collagenous materials suitable as starting compounds for the method according to the invention are for example described in U.S. Pat. No. 5,397,353 and U.S. Pat. No. 6,936,271.

The acidic solution of step a) of the method according to the invention is generally prepared by solubilization of non-antigenic collagenous material in powder or fibrous form in water. The solution is adjusted to the desired pH, for example by adding chlorohydric acid or acetic acid, either before or after introduction of the non-antigenic collagenous material. In one embodiment of the method according to the invention, the pH of the solution is adjusted to a value ranging from about 2.0 to about 4.0, preferably from about 3.0 to about 3.5, more preferably to about 3.4, for example by adding chlorohydric acid or acetic acid.

Such pHs for the solution of step a) make it possible to obtain, in the end, matrices which have particularly good tensile strength.

In one embodiment of the method according to the invention, the solution of step a) is a solution of non-antigenic collagenous material in acidic water, the concentration of non-antigenic collagenous material in said solution ranging from 0.1 to 10%, preferably from 0.5% to 3%, and more preferably about 1% by weight, relative to the total weight of the solution.

Such concentrations make it possible to obtain, in the end, matrices which have particularly good tensile strength. Also preferably, the solution of the method according to the invention is free of any other polymer than the non-antigenic collagenous material.

According to a second step of the method according to the invention, step b), the acidic solution of non-antigenic collagenous material is poured into a mould in order to form a layer. Generally, the mould is in the shape of a rectangle having dimensions compatible with the use of the matrix obtained as all or part of a reinforcing implant for the abdominal wall or of a haemostatic patch.

According to a third step of the method according to the invention, step c), the layer obtained in b) is lyophilized so as to obtain a matrix.

In the present application, the term "matrix" is intended to mean a layer which has pores, or gaps, alveoli, holes, orifices, which are evenly or unevenly distributed not only at the surface, but also within the thickness of said layer, and which are more or less interconnected, depending on the lyophilization process used. Such lyophilization processes are known. It is known practice to vary the freezing temperature and speed and also the characteristics of the polymer solution to be lyophilized (pH, concentration, etc.), in this case non-antigenic collagenous material, as a function of the structure of the matrix that it is desired to obtain (see U.S. Pat. No. 4,970,298; Doillon et al, J Biomed Mater Res, 1986; Schoof, J Biomed Mater Res, 2001; O'Brien et al, Biomaterials, 2004).

In embodiments, in step c), the layer is frozen during a time ranging from 3 to 15 hours. In embodiments, in step c), the frozen layer is primary dried during a time ranging from 7 to 15 hours.

The matrix obtained by the lyophilization of the layer of acidic solution of non-antigenic collagenous material is acidic, in other words has an acidic extractible pH. Such an extractible pH may vary from 3 to 5, and for example is 4.

According to a fourth step of the method according to the invention, step d), the matrix obtained in c) is sterilized with ethylene oxide.

In a first stage of the sterilization step, the matrix may be preconditioned in order to make sure that it is at a uniform temperature and humidity. In this view, the matrix is put in a cell and may be exposed during a determined time, ranging for example from 8 to 15 hours, to a warm and humid environment. The temperature may range from about 28° C. to about 32° C. The relative humidity may range from about 50 to about 80%.

In a second stage of the sterilization process, the cell is evacuated and the ethylene oxide is introduced. In embodiments, in step d), the matrix is exposed to ethylene oxide for a time that may range from about 10 to about 11 hours. During this time, a certain amount of ethylene oxide, for example from 1.6 to 2 kg, is injected. In embodiments, in step d), the ethylene oxide is injected at a pressure that may range from 70000 Pa to 78000 Pa. The temperature and relative humidity may be the same as in the first stage.

In a third stage, ethylene oxide is removed and air replaces the ethylene oxide in the cell.

At the end of the sterilization step, the sterilized matrix of non-antigenic collagenous material may show an extractible pH of about 7.0-7.4.

This sterilization step has as a consequence that the pH of the matrix of non-antigenic collagenous material is increased to about 7.0-7.4, in particular is increased from about 3.0-4.0 to about 7.0-7.4. The sterilized matrix is therefore neutralized during the sterilization with the ethylene oxide.

The sterilization and the neutralization of the matrix therefore occur in one single step. The method of the invention therefore allows saving an operation step with respect to methods of the prior art in which the sterilization step and the neutralization step are two separate operations.

The matrix of non-antigenic collagenous material which has been neutralized and sterilized according to the method of the invention can be part of, or constitute, the whole of a surgical implant, for example an abdominal wall reinforcement or of an haemostatic patch. Indeed, these neutralized and sterilized matrices have excellent tensile strength.

Another aspect of the invention relates to a surgical implant, such as an abdominal wall reinforcement, for example a hernia repair implant, or an haemostat such as a haemostatic patch, comprising at least one neutralized matrix of non-antigenic collagenous material obtained by the method described above. An aspect of the invention relates to a hernia repair implant comprising at least one neutralized matrix of non-antigenic collagenous material obtained by the method described above. For example, the hernia repair implant may consist in a neutralized matrix of non-antigenic collagenous material obtained by the method described above. An aspect of the invention relates to a haemostat comprising at least one neutralized matrix of non-antigenic collagenous material obtained by the method described above. For example, the haemostat may consist in a neutralized matrix of non-antigenic collagenous material obtained by the method described above.

Another aspect of the invention is a method for increasing the tensile strength of a matrix of non-antigenic collagenous obtained by:
 a) preparing an acidic solution of non-antigenic collagenous material,
 b) pouring the solution of a) into a mould in order to form a layer,
 c) lyophilizing the layer of b) in order to obtain an acidic matrix of non-antigenic collagenous material,
said method comprising the step of sterilizing the acidic matrix obtained in c) with ethylene oxide.

The invention and the advantages thereof will emerge more clearly from the example below and the appended FIGURE in which:

FIG. 1 is a graph comparing the tensile strengths of a matrix obtained with the method of the invention and of two other matrices not obtained with the method of the invention.

EXAMPLE 1

Non-antigenic collagenous material, similar to that described at example 5 of U.S. Pat. No. 6,936,271, except for the crosslinking step, is provided, under the form of powder.

A solution of non-antigenic collagenous material at 1% (w/w) in water is prepared and adjusted to about pH 4.0 by addition of HCl.

121 g of this solution is poured into a rectangular mould of dimensions of 12 cm×17 cm, so as to form a layer of the solution.

The layer is lyophilised for about 24 hours, with a freezing step of 4 hours, and a primary drying step of 8 hours.

A matrix of non-antigenic collagenous material is obtained. This matrix is acidic, i.e. this matrix has an extractible pH of about 5.2.

The matrix is then sterilized with ethylene oxide according to the following process.

In a first stage, the matrix is put in a cell and is exposed during 8-15 hours to a warm and humid environment with the following parameters:

Temperature: 28-32° C.

Relative humidity: 50-80%

In a second stage, the cell is evacuated and the ethylene oxide is introduced. The matrix is exposed to ethylene oxide for approximately 10-11 hours. During this time, 1.6 to 2 kg of ethylene oxide is injected. The ethylene oxide injection pressure ranges from 70000 to 78000 Pa. The temperature and relative humidity are the same as in the first stage.

In a third stage, ethylene oxide is removed.

The sterilized matrix obtained shows an extractible pH of about 7.0. As a consequence, the sterilization of the matrix with ethylene oxide has led to an increase of the extractible pH of the matrix from about 5.2 to about 7.0.

The sterilized matrix of non-antigenic collagenous material is therefore neutralized. Such a matrix may be used for the manufacture of a surgical implant such as an abdominal reinforcement or a haemostatic patch with no risk that the matrix dissolves or collapses at the contact of a neutral medium such as the biological fluid.

In addition, the sterilized and neutralized matrix obtained shows very good tensile strength. In particular, the sterilized matrix shows a higher tensile strength than the non sterilized matrix.

Comparative Tests:

The tensile strengths of the matrix of the present example before sterilization (comparative referenced N/A), after sterilization with ethylene oxide (invention referenced EtO), and of a matrix of same composition of that of the present example but neutralized with ammonia (comparative reference Ammonia) have been measured according to the test described in standard ASTM D0638-03 with type IV specimen.

With reference to FIG. 1, are shown:

the tensile strength of the matrix of the present example before sterilization (reference N/A on the graph), the tensile strength of the matrix of the present example after sterilization with ethylene oxide (referenced EtO on the graph), and the tensile strength of a matrix of same composition of that of the present example but neutralized with ammonia (referenced Ammonia).

The results are collected in the following table:

| Sample | N/A (comparative) | EtO (invention) | Ammonia (comparative) |
|---|---|---|---|
| Tensile strength in Newton | 0.15 | 0.50 | 0.28 |

As shown on this graph, the tensile strength of the matrix obtained by the method of the invention is at least two times, and is even about three times, greater than that of the non sterilized matrix. In addition, the tensile strength of the matrix obtained by the method of the invention is about twice greater than that of a matrix neutralized by Ammonia.

EXAMPLE 2

Non-antigenic collagenous material, similar to that described at example 5 of U.S. Pat. No. 6,936,271, except for the crosslinking step, is provided, under the form of powder.

A solution of non-antigenic collagenous material at 1% (w/w) in water is prepared and adjusted to about pH 3.4 by addition of $CH_3COOH$.

121 g of this solution is poured into a rectangular mould of dimensions of 12 cm×17 cm, so as to form a layer of the solution.

The layer is lyophilised for about 24 hours, with a freezing step of 4 hours, and a primary drying step of 8 hours.

A matrix of non-antigenic collagenous material is obtained. This matrix is acidic, i.e. this matrix has an extractible pH of about 5.1.

The matrix is then sterilized with ethylene oxide according to the following process.

In a first stage, the matrix is put in a cell and is exposed during 8-15 hours to a warm and humid environment with the following parameters:

Temperature: 28-32° C.

Relative humidity: 50-80%

In a second stage, the cell is evacuated and the ethylene oxide is introduced. The matrix is exposed to ethylene oxide for approximately 10-11 hours. During this time, 1.6 to 2 kg of ethylene oxide is injected. The ethylene oxide injection pressure ranges from 70000 to 78000 Pa. The temperature and relative humidity are the same as in the first stage.

In a third stage, ethylene oxide is removed.

The sterilized matrix obtained shows an extractible pH of about 7.0-7.4. As a consequence, the sterilization of the matrix with ethylene oxide has led to an increase of the extractible pH of the matrix from about 5.1 to about 7.0-7.4.

The sterilized matrix of non-antigenic collagenous material is therefore neutralized. Such a matrix may be used for the manufacture of a surgical implant such as an abdominal reinforcement or a haemostatic patch with no risk that the matrix dissolves or collapses at the contact of a neutral medium such as the biological fluid.

The tensile strengths of the matrix of the present example before sterilization and after sterilization with ethylene oxide have been measured according to the test described in standard ASTM D0638-03 with type IV specimen.

The results are collected in the following table:

| Sample | Matrix (before sterilization) | Matrix (after EtO sterilization) |
|---|---|---|
| Tensile strength in Newton | 0.28 | 0.78 |

As shown on this graph, the tensile strength of the matrix obtained by the method of the invention is at least twice, and is even about 2.8 times, greater than that of the non sterilized matrix.

The invention claimed is:

1. A method for preparing a neutralized matrix of non-antigenic collagenous material comprising:
   a) preparing an acidic solution of non-antigenic collagenous material, wherein a pH of said acidic solution is adjusted to a value ranging from about 2.0 to about 4.0,
   b) pouring said acidic solution of a) into a mold in order to form a layer,
   c) lyophilizing said layer of b) in order to obtain an acidic matrix of non-antigenic collagenous material,
   d) sterilizing said acidic matrix obtained in c) with ethylene oxide in order to obtain a neutralized matrix of non-antigenic collagenous material.

2. The method according to claim 1, wherein said acidic solution of step a) is a solution of non-antigenic collagenous material in acidic water, said non-antigenic collagenous material concentration in said acidic solution ranging from 0.1 to 10% by weight, relative to a total weight of said acidic solution.

3. The method according to claim 2, wherein said non-antigenic collagenous material concentration in said acidic solution ranges from 0.5% to 3% by weight, relative to a total weight of said acidic solution.

4. The method according to claim 2, wherein said non-antigenic collagenous material concentration in said acidic solution is 1% by weight, relative to a total weight of said acidic solution.

5. The method according to claim 1, wherein said pH of said acidic solution in a) is adjusted to a value ranging from about 3.0 to about 3.5.

6. The method according to claim 1, wherein said pH of said acidic solution in a) is adjusted to a value of about 3.4.

7. The method according to claim 1, further comprising adding chlorohydric or acetic acid to said acidic solution of step a).

8. The method according to claim 1, wherein said acidic solution of step a) is free of any other polymer than the non-antigenic collagenous material.

9. The method according to claim 1, wherein said lyophilizing of said layer in c) comprises freezing said layer during a time ranging from 3 to 15 hours to form a frozen layer.

10. The method according to claim 9, wherein said frozen layer is primarily dried during a time ranging from 7 to 15 hours.

11. The method according to claim 1, wherein said sterilizing the acidic matrix in d) comprises exposing said acidic matrix to ethylene oxide for a time ranging from about 10 to about 11 hours.

12. The method according to claim 1, wherein said ethylene oxide is injected at a pressure ranging from 70000 Pa to 78000 Pa.

13. A surgical implant comprising at least one neutralized matrix of non-antigenic collagenous material obtained by the method of claim 1.

14. The surgical implant according to claim 13, wherein the at least one neutralized matrix of non-antigenic collagenous material comprises a tensile strength at least two times greater than that of a non-sterilized matrix of non-antigenic collagenous material.

15. The surgical implant according to claim 14, wherein said tensile strength is about three times greater than that of a non-sterilized matrix of non-antigenic collagenous material.

16. The surgical implant according to claim 13, wherein the surgical implant is a hernia repair implant.

17. The surgical implant according to claim 13, wherein the surgical implant is a haemostat.

18. The surgical implant according to claim 13, wherein the at least one neutralized matrix of non-antigenic collagenous material comprises a tensile strength of 0.5 N.

* * * * *